United States Patent
Pyo

(10) Patent No.: US 8,961,963 B2
(45) Date of Patent: Feb. 24, 2015

(54) PHARMACOLOGICAL COMPOSITION WHEREBY STATIN AND COQ10 COMPOUNDS ARE ENHANCED

(75) Inventor: Young-Hee Pyo, Gwangju-si (KR)

(73) Assignee: Sungshin Women's University Industry-Academic Cooperation Foundation, Seoul (KR)

( * ) Notice: Subject to any disclaimer, the term of this patent is extended or adjusted under 35 U.S.C. 154(b) by 47 days.

(21) Appl. No.: 13/501,841

(22) PCT Filed: Dec. 28, 2009

(86) PCT No.: PCT/KR2009/007845
§ 371 (c)(1),
(2), (4) Date: Oct. 1, 2012

(87) PCT Pub. No.: WO2011/046258
PCT Pub. Date: Apr. 21, 2011

(65) Prior Publication Data
US 2013/0017187 A1    Jan. 17, 2013

(30) Foreign Application Priority Data
Oct. 15, 2009    (KR) ........................ 10-2009-0098443

(51) Int. Cl.
| | | |
|---|---|---|
| *A61K 35/00* | (2006.01) | |
| *C12P 1/00* | (2006.01) | |
| *C12P 7/66* | (2006.01) | |
| *A61K 31/122* | (2006.01) | |
| *A61K 36/062* | (2006.01) | |
| *A61K 45/06* | (2006.01) | |
| *C12P 17/06* | (2006.01) | |

(52) U.S. Cl.
CPC .................. *C12P 7/66* (2013.01); *A61K 31/122* (2013.01); *A61K 36/062* (2013.01); *A61K 45/06* (2013.01); *C12P 17/06* (2013.01)
USPC .............. 424/115; 435/41; 435/171; 435/133

(58) Field of Classification Search
None
See application file for complete search history.

(56) References Cited

U.S. PATENT DOCUMENTS

| | | | | |
|---|---|---|---|---|
| 5,627,068 | A * | 5/1997 | Kujumdzieva et al. | 435/254.1 |
| 5,744,350 | A * | 4/1998 | Vinci et al. | 435/254.11 |
| 6,632,428 | B1 * | 10/2003 | Zhang et al. | 424/93.51 |
| 2005/0153406 | A1 * | 7/2005 | Murata et al. | 435/133 |
| 2006/0147717 | A1 * | 7/2006 | Hasegawa et al. | 428/412 |
| 2009/0036693 | A1 * | 2/2009 | Nagano et al. | 552/307 |
| 2009/0148433 | A1 * | 6/2009 | Naidu et al. | 424/94.61 |
| 2010/0021582 | A1 * | 1/2010 | Kwon | 426/11 |
| 2013/0011384 | A1 * | 1/2013 | Morgavi et al. | 424/115 |

FOREIGN PATENT DOCUMENTS

KR    10-0734612    *    7/2007    .............. A23L 1/202

OTHER PUBLICATIONS

Pisareva et al., Biotechnol. & Biotechnol. 20(1): 88-96 (2006).*
Lin et al., Appl. Microbiol. Biotechnol., 77:965-973 (2008).*
Pattanagul et al., Intl. J. Food Microbiol., 126:20-23 (2008).*

\* cited by examiner

*Primary Examiner* — Blaine Lankford
*Assistant Examiner* — Thomas J Visone
(74) *Attorney, Agent, or Firm* — Michael B. Fein, Esq.; Eckert Seamans Cherin & Mellott, LLC

(57) ABSTRACT

Disclosed is a pharmaceutical natural composition containing both statin compounds (mevinolin and mevinolinic acid) serving as cholesterol biosynthesis inhibitors and coenzyme Q (ubiquinone-10: CoQ10 and ubiquinone-9: CoQ9) compounds which are substances that inhibit factors causing complications such as myalgia involved in long-term use of the statin, prepared using *Monascus* sp. and natural medicinal substances such as *ginseng*, mushrooms and cereals.

6 Claims, 3 Drawing Sheets

PHARMACOLOGICAL COMPOSITION WHEREBY STATIN AND COQ10 COMPOUNDS ARE ENHANCED

CROSS-REFERENCE TO RELATED APPLICATIONS

The present application is a 35 U.S.C. 371 National Stage Application of International Application No. PCT/KR2009/007845, International Filing Date: Dec. 28, 2009, which claims priority under 35 U.S.C. §119(a) to Korean Application No. 10-2009-0098443, Filing Date: Oct. 15, 2009, each of which are incorporated herein by reference in its entirety.

BACKGROUND OF THE INVENTION

1. Field of the Invention

The present invention relates to a method for preparing a natural pharmaceutical composition that contains both statin acting as a cholesterol biosynthesis inhibitor, and a CoQ10 compound as a substance that inhibits factors causing complications involved in oral administration of the statin, thus exhibiting multi-physiological active functions such as anti-arteriosclerosis and cardiac function reinforcement, through fermentation using *Monascus* sp. and natural substances having pharmaceutical efficacies.

2. Description of the Related Art

Coenzyme Q10 (ubiquinone, CoQ10) is a quinone substance similar to fat-soluble vitamins, which are present throughout human tissues. The major biochemical function of Coenzyme Q10 is as an electron carrier in intracellular energy (ATP) metabolism in cellular respiration of mitochondriona (Sarah L. Molyneux et al., Journal of the American College of Cardiology, 52, 1435-1441, 2008). Also, Coenzyme Q10 functions as an endogenous antioxidant preventing oxidative damage of cellular membranes and removing reactive oxygen species and the like. CoQ10 is vigorously biosynthesized in the twenties in humans and biosynthesis thereof decreases with age. Accordingly, research into industrial mass-production of CoQ10 and utilization of the same in a variety of applications including medicines, functional health functional foods, and cosmetics has been conducted (Littarru et al., Nutr. Res., 42, 291-305, 1972; Khatta M et al., Ann Intern Med, 132, 636-640, 2000). 90% or more of CoQ10 present in human serum and organism tissues is a reduced form of ubiquinol (ubiquinol, $CoQ10H_2$) which is a potent fat-soluble antioxidant. A ratio of $CoQ10H_2$:CoQ10 and a decrease in serum CoQ10 are related to oxidative stress. Oxidative stress defined by disequilibrium between prooxidants and antioxidants is known to be a major risk factor related to pathologic conditions such as cardiovascular disease, diabetes and cancer as well as aging (S. Yamashita et al., Anal Biochem, 250, 66, 1997; D. Steinberg et al., Engld J Med, 320, 915, 1989). In particular, a ratio of ubiquinol and ubiquinone, both of which are CoQ10 is commonly used as a reference value in a great deal of research associated with the prevention, diagnosis and treatment of oxidative damage. Oxidation of plasma lipoprotein is a major cause of arteriosclerosis as well as other diseases associated with free radicals such as Parkinson's disease, Alzheimer's disease or beta-thalacemia. In this case, ubiquinol removes peroxy radicals, reduces alpha-tocopheryl radicals and thereby prevents oxidation of LDL. In fact, as compared to alpha-tocopherols acting as plasma antioxidants, ubiquinol is an endogenous antioxidant that first reacts with plasma, regardless of concentration, when the plasma is exposed to the antioxidant. Accordingly, use of supplements in order to reinforce CoQ10 is beneficial in the enhancement of human health. Intake of CoQ10 via foods or food supplements increases a level of CoQ10 in blood and helps reinforce antioxidant functions, thus preventing onset of major diseases caused by cellular oxidative damage.

A great deal of research to identify relation between CoQ10 deficiency, disease conditions, clinical improvement after administration of CoQ10 and the like has been made. First of all, it was demonstrated that CoQ10 is efficacious in lengthening statin treatment without side effects and maintaining an essential cellular bio-energy amount when it is supplemented to hypercholesterinemia patients who should take statin drugs for a long period of time. Statin that was first developed in 1987 has contributed to decrease cardiovascular diseases, as a first-generation cholesterol inhibitor. However, commonly, humans expect to develop a second-generation cholesterol suppressor that has more specific actions while not interfering with biosynthesis of other compounds, like CoQ10. Accordingly, if drugs (supplements) consisting of natural substances containing predetermined concentrations or higher of both statin and CoQ10 which are natural anticholesterol components have been developed, side effects of statin which is an anti-cholesterol drug are removed through additional or synergistic treatment effects between these compounds and health benefits can be obtained through bio-activity enhancement of CoQ10.

All over the world, coronary artery diseases are considered to be major mortality factors and, in particular, hypercholesterinemia is considered to be the most risk factor.

$\frac{2}{3}$ or higher of total cholesterol in humans is obtained by biosynthesis. In the biosynthesis, a step on which an HMG-CoA reductase (3-hydroxy-methyl-3-glutaryl-coenzyme reductase) acts is an initial step and, at the same time, is a step that limits a speed of synthesis route (FIG. 3).

HMG-CoA reductase inhibitors globally used in recent years, that is, statin (or mevinolin, lovastatin, monacolin K, Mevacor, $C_{24}H_{36}O_5$) drugs have been used for a long period of time in order to effectively treat hypercholesterinemia and prevent death caused by cardiovascular diseases. Statin drugs are considerably potent substances that directly inhibit biosynthesis of endogenous cholesterol corresponding to 80% of total cholesterol, but statin drugs are classified into special medicines that are sold in the presence of a medical prescription, since an activation process in which the ring of molecular structures is opened by hydrolase (carboxyesterase) causes damage to the liver and kidneys, as well as side effects such as myopathy (Thomson P D et al., JAMA. 289: 1681-1690 2003). However, statins inhibit HMG-CoA reductases and thereby reduce production of cholesterol, while they have the same biosynthesis route as ubiquinone, which are in-vivo electron and quantum carriers and thus affect biosynthesis of cholesterol as well as CoQ10, resulting in deterioration in yields of two substances (FIG. 3). That is, unfortunately, potential impacts of statins at a mevalonate-level are unspecific and, as a result, statins inhibit biosynthesis of various sterol isoprenoids including CoQ10 and dolichol. Accordingly, patients who take statin for a long period of time are known to suffer from side effects such as myalgia, since a level of biosynthesized CoQ10, which plays a role as an essential factor in the energy production of mitochondriona, in the blood is increased. That is, use of statins decreases a concentration of CoQ10 in plasma, increases a ratio of lactic acid to pyruvic acid and, furthermore, deteriorates functions of mitochondriona respiration system. As a consequence, deficiency of energy production increases a fatigue degree of muscles and thus decreases aerobic capacity (respiration capacity).

Accordingly, use of statin drugs for a long period of time is found to deteriorate cardiac function and blood circulation due to decrease in level of CoQ10 in the blood, thus resulting in serious side effects. That is, statin drugs are reported to cause side effects of digestive systems (such as constipation, diarrhea, dyspepsia, abdominal inflation and abdominal pain) and side effects of nervous systems (such as dizziness and headache) and side effects such as skin rashes and visual disturbances. In particular, side effects such as liver failures are proved to be serious to an extent that patients stop taking their statin drugs, and development of a method for maintaining a concentration of CoQ10 in the blood of statin users at a predetermined level was demanded. In this regard, U.S. Pat. No. 5,082,650 discloses that a correlation between variation in concentration of CoQ10 in the blood and side effects in various cases is observed with respect to patients, to which statin drugs (MEVACOR) are applied, a correlation between the concentration of CoQ10 in the blood, and reduction and removal of side effects through supplementing with CoQ10 is discovered and prescription of CoQ10 is also required for users of statin drugs. Accordingly, it is found that statin drugs used in order to maintain the concentration of cholesterol in the blood should be administered in combination with supplement of CoQ10 (200 mg per day) to prevent serious side effects generated in the heart and liver.

For this purpose, similar research results to execute the US patent are disclosed in Korean Patent Laid-open No. 2009-28983. This patent discloses a multi-therapeutic pharmaceutical composition for oral administration, containing both statin drugs and coenzyme 10 as synthetic medicines in order to prevent side effects of the statin drugs which are synthetic medicines for treating hyperlipidemia, wherein the composition contains a great amount of a solubilizer such as polyethylene glycol to increase solubility of water-insoluble lactone-type synthetic statin, a surfactant, an oil to provide an emulsion, a sodium or calcium antioxidant to secure stability, a pH adjuster or the like.

However, statin drugs and CoQ10, main components of the substance, are artificially synthesized compounds, which are water-insoluble and thus have problems of solubility in the intestine. In particular, calcium salt medicines, pH, of which is adjusted to 6.7, have a problem of considerably low solubility.

However, the present invention is designed under the assumption that all the problems can be solved, if an acid-form natural statin compound having a pH of 6.5 to 7.0 is bio-synthesized by natural fermentation.

To date, Monascus sp. (red yeast rice red koji) is prepared by inoculating rice with the genus Monascus (red mold fungi), which has been used as natural food colorings or products or substances for digestion promotion and blood stream improvement in various East Asian nations including China for a long time. In particular, it was reported that natural statins (HMG-CoA reductase inhibitors) which are secondary metabolites produced by Monascus sp. potently inhibit HMG-CoA reductases, cholesterol biosynthesis enzymes, and thus exhibit functionalities of various bioactivities, based on deterioration in blood-lipid concentration and cholesterol biosynthesis (Wang I K et al., J. Agri. Food Chem. 48: 3183-3189 2000; Endo A. et al., J. Antibiotechnol. 38: 420-422 1985; Manzoni M & Rollini M. App. Microbiol. Biotechnol. 58: 555-564 2002; Wei W. et al., J. Nutri. Biochem. 14: 314-318 2003). Since then, Monascus sp. has been widely used as an herbal medicine in Chinese "medicine".

Meanwhile, to date, submerged fermentation of liquid culture has generally been used for production of Monascus sp. cultures. Optimum fermentation conditions to obtain a pigment component and statin (mevinolin) as functional metabolites, strain search, and preparation of functional products containing Monascus sp. have been studied. Also, solid fermentation is also used in order to obtain functional components including pigments, but it is known that a main cereal of used medium is rice, barley and wheat are also used, and bean (white bean) is unsuitable for use in a Monascus sp. solid medium due to high protein content. However, the inventors of the present invention established fermentation conditions using bean, as a substrate for a solid medium, instead of rice, developed a method for producing statins derived from Monascus sp. fermented with bean, and obtained first patents in Korea as well as other nations (Korean Patent No. 0734612). However, this invention only aims at successively producing Monascus sp. fermented with bean without producing citrinin that acts as a kidney or liver toxin by fermenting Monascus sp., using bean, instead of rice, for preparation of a solid medium for statin (mevinolin) biosynthesis.

In order to overcome the limitations of medium preparation, the present inventors provide a safe and improved natural pharmaceutical composition for preventing and treating hyperlipemia wherein a biosynthesized statin amount is increased by 10% or more and a great amount of CoQ10 is simultaneously accumulated, by remarkably changing a composition of a seed culture. Furthermore, the present inventors attempt to identify biosynthesis of Monascus sp.-derived citrinin that acts as a toxic component that causes functional disorders of kidney and liver, as mold metabolites in in vivo pharmaceutical functional mechanisms.

Conventional methods associated with the specific medium composition of Monascus sp. of the present invention and simultaneous biosynthesis of the multi-physiologically active substance of the present invention include Korean Patent Laid-open No. 2005-13188 that discloses a composition containing statin for treating leukemia, Korean Patent Laid-open No. 2007-7022964 that discloses treatment using statin, omega-3 fatty acid and a combination thereof, Korean Patent Laid-open No. 2007-7003811 that discloses a novel statin pharmaceutical composition and a method for treating diseases associated therewith, Korean Patent Laid-open No. 2007-7000831 that discloses a composition containing statin and a bronchodilator, Korean Patent Laid-open No. 2006-7015689 that discloses a composition for treating hypocholesterolemia containing a statin and a de-gassing agent, and Korean Patent Laid-open No. 2009-7004090 that discloses a pharmaceutical composition containing statin-capsulated nanoparticles. However, it could not identified that the conventional patents deny novelty and inventive step of the present invention, with respect to liquid culture media associated with simultaneous biosynthesis of statin and CoQ10, as natural combined physiologically active substances, and simultaneous production methods for these substances.

SUMMARY OF THE INVENTION

Therefore, the present invention has been made in view of the above problems, and it is one object of the present invention to provide a liquid culture medium that enables biosynthesis of both statin and ubiquinone as natural combined physiologically active substances.

It is another object of the present invention to provide a solid fermentation product reinforced with both compounds, obtained by inoculating a liquid culture fermented with the discovered liquid medium, as a seed culture, in a solid medium containing a mixture of various natural cereal substances, followed by fermentation for a predetermined period of time.

It is another object of the present invention to provide a health functional food or a composition containing the solid fermentation product, to reduce side effects of natural statin drugs and to prevent and treat cardiovascular diseases.

The aspects of the present invention are achieved by a process including: providing a natural liquid culture medium for preparing a combined physiologically active compound that contains both statin acting as a cholesterol biosynthesis inhibitor and a CoQ10 compound which inhibits factors causing complications involved in oral administration of the statin, to exhibit multi-physiological active functions such as anti-arteriosclerosis and cardiac function reinforcement, using *Monascus* sp. and natural substances having pharmaceutical efficacies; selecting superior strains using the liquid medium; obtaining a liquid culture of *Monascus* sp. using the medium; inoculating a solid medium with the liquid culture, followed by fermentation for a predetermined period of time to increase combined physiologically active substances of natural statin and ubiquinone; and evaluating a chemical structure of the produced combined physiologically active substance.

Hereinafter, although disclosures of the present invention will be described with reference to examples in detail, simple modification of solid medium components consisting of a medicinal liquid medium and a cereal mixture, and simple design modification of solid fermentation fall within the scope of the present invention.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION OF THE INVENTION

Figure 1:
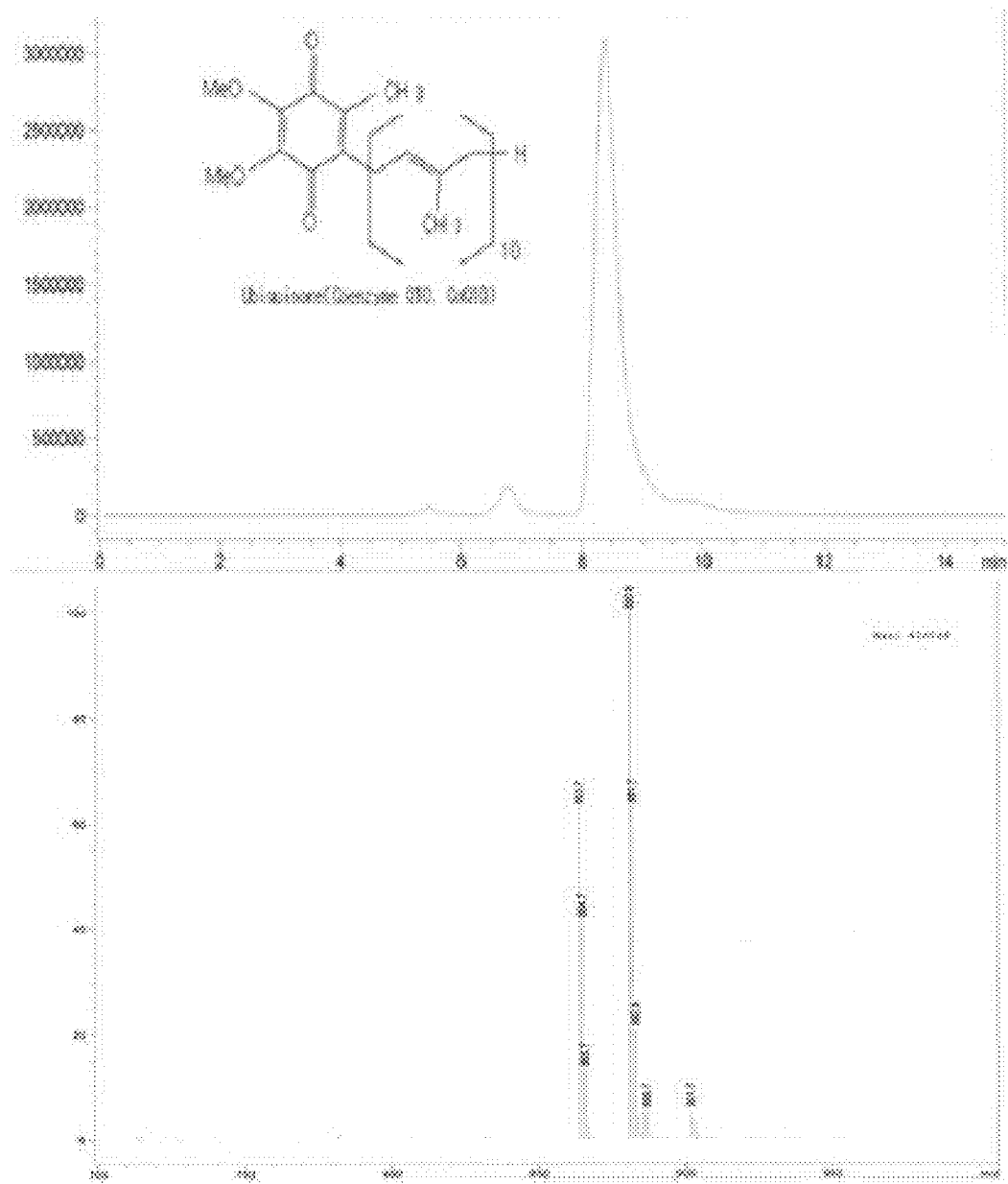
FIG. 1 illustrates a chemical structure and an LC-MS spectrum of CoQ9.

The present invention comprises adding *Monascus* sp. together with medicinal natural substances such as *ginseng* and mushroom to a liquid medium containing a rice powder to prepare a liquid culture as a primary fermentation solution or inoculating a solid medium containing a cereal mixture with the seed culture to prepare a solid fermentation product as a secondary fermentation solution.

In the present invention, the medicinal natural substances mean ginsengs, paprikas, mushrooms, tomatoes and include processed and unprocessed materials, and bio-synthesized forms of major natural compounds such as natural statin and ubiquinone. In this case, as a result of tests, most preferably, a *ginseng* powder is 1 to 2%, paprika is 0.5 to 1.5%, a mushroom powder is 0.5 to 1.5%, and a tomato powder is 0.5 to 1.5% (w/v). The present invention includes a method for producing a combined physiologically active composition containing both natural statin and a ubiquinone compound wherein *Monascus* sp. is selected from *Monascus anka, Monascus purpureus, Monascus pilosus, Monascus kaoliang, Monascus ruber, Monascus vitreus* and a combination thereof.

The present invention provides a method for producing a combined physiologically active composition containing both natural statin and a ubiquinone compound wherein the statin and the ubiquinone compound are superior strains among the *Monascus* sp.

Also, the present invention provides a method for producing a combined physiologically active composition containing both natural statin and a ubiquinone compound, wherein the *Monascus* sp. seed culture is obtained by inoculating a nutriment medium containing one or more medicinal natural substances of ginsengs, mushrooms, paprikas and tomatoes, with *Monascus* sp. cultured in a PDA medium, followed by culturing.

The present invention provides a method for simultaneously producing mevinolin and ubiquinone, wherein the natural liquid medium comprises 2% to 10% of a rice powder, 0.5% to 2.0% of a peptone, 1% to 5% of glycine, 6% to 20% of glucose, and 0.1% to 1.0% of a meat extract, in which percentage (%) is based on w/v, the medicinal natural comprises 0.5% to 1.5% of a *ginseng* powder, 0.5% to 1.5% of a red paprika powder, 0.5 to 1.5% of a mushroom powder, and 0.5% to 1.5% of a tomato powder in which percentage (%) is based on w/v (w/v) and an initial pH of the medium is 6.0±0.5.

The present invention focuses on development of using a natural pharmaceutical composition containing statin as an anti-cholesterol component and coenzyme CoQ10 which is an endogenous fat-soluble antioxidant and prevents side effects of statin drugs, as main compounds, using medicinal natural substances and genus *Monascus* strains which were not been tried to date and medicinal materials suitable for production of the composition.

First, a culture medium is prepared as a nutrient medium that targets 15 species of the genus, *Monascus* strains and amounts of produced statin and ubiquinone are evaluated. The present inventors attempted only to establish conditions that do not produce citrinin as a toxic substance to determine optimum liquid medium composition for liquid fermentation and concentrations of components, since the solid fermentation as a secondary fermentation performed by applying a liquid culture used for *Monascus* sp. fermentation to bean (white bean) aims only at normal fermentation and beans having a higher protein content than a sugar content have unfavorable fermentation conditions for successful *Monascus* sp. fermentation due to component composition, as compared to rice materials.

However, in accordance with the present invention, medicinal natural substances are variously researched and selected, optimum contents to obtain liquid medium conditions are determined, a liquid medium is inoculated with a *Monascus* sp. strain, followed by culturing, biosynthesis of physiologically active substances, i.e., statin and ubiquinone which are target substances of the present invention, in the liquid culture sample are analyzed and evaluated to select superior strains, and solid fermentation is performed using the liquid culture as a culture medium, and a single grain or a combination thereof, as a solid medium, as compared to liquid composition. The present invention aims at providing a medicinal natural composition that has increased concentrations of two physiologically active components, as compared to a liquid composition, during solid fermentation.

Figure 2:
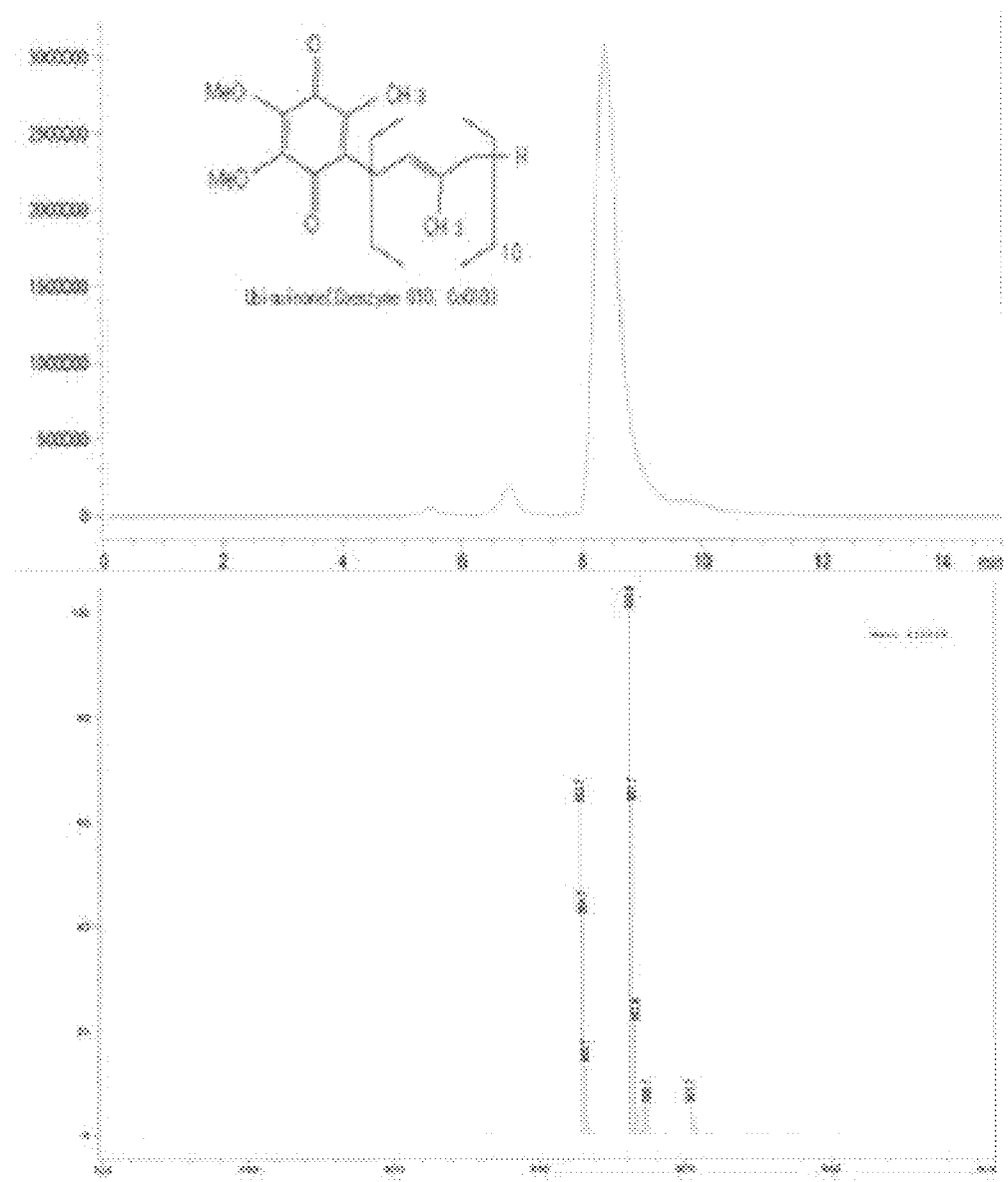
FIG. 2 illustrates a chemical structure and an LC-MS spectrum of CoQ10.
Figure 3:
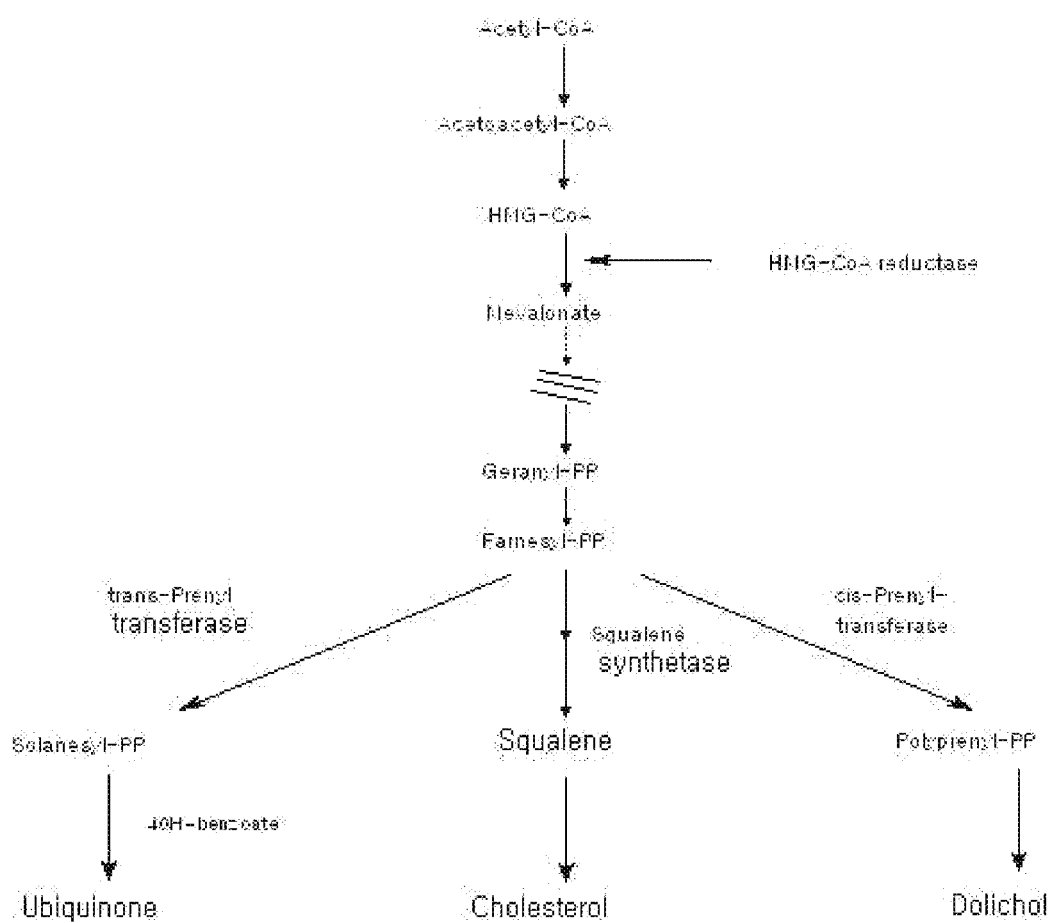
FIG. 3 is a flowchart illustrating biosynthesis of statin (mevinolin) and ubiquinone.

Accordingly, the most creative features of the present invention are selection of superior strains, preparation of medicinal liquid culture containing both statin and ubiquinone, and solid fermentation including inoculating the liquid culture in a solid medium such as single grain or a grain mixture, to prepare a secondary fermentation product having increased concentrations of physiologically active substances. The natural substance components used for preparation of the liquid culture medium have molecular structures containing an isoprene unit or a benzoquinone nucleus in common, thus reinforcing and facilitating ubiquinone biosynthesis metabolisms of *Monascus* strain containing ubiquinone systems (FIGS. 1 to 2). Accordingly, the present fermentation is a unique fermentation that efficiently produces metabolites of target substances, i.e., ubiquinone and statin (FIG. 3).

The present invention comprises preparing a medicinal liquid composition containing statin and ubiquinone using predetermined amounts of *Monascus* sp. and natural substance powders. In this case, natural substances include mushrooms, ginseng, paprika, and tomatoes that have a molecular structure containing an isoprene unit or a benzoquinone nucleus and may be selected from a naturally dried powder, a processed powder and a combination thereof.

The materials used for preparation of the medicinal natural composition in Examples of the present invention were obtained from a market in Garak-dong, Seoul, Korea. Also, strains of the identified genus of *Monascus* were obtained from the Korea Food Research Institute and used for selection of superior strains.

The natural substances used as samples for liquid culture in the present invention were added at a predetermined ratio after being washed with water, suitably trimmed, lyophilized and powdered.

Grains used for solid fermentation in the present invention were immersed in water for 5 to 15 hours, water was removed from the grains, the grains were added at a weight of about 100 g (having a water content of 35 to 45%) to a 500 mL Erlenmeyer flask, sealed with a natural current, which was then used as the subsequent process.

The cereal sample containing polished nonglutinous rice, barley, wheat, sorghum, and millet singly or a combination thereof at a mix ratio (weight ratio) at 1:1:1:1:1 was prepared to complete the present invention.

*Monascus* sp. strains used for the present invention were cultured in a potato dextrose agar (PDA) medium at 30±5° C. for 3 to 4 days and were used for seed cultures. The *Monascus* sp. culture is homogenized in a liquid medium containing rice powder, peptone, glycine, and glucose and a powder of medicinal natural substances, the *Monascus* sp. culture was inoculated at an amount of 5 to 10% (v/w) of the sample weight as the seed culture, and shake-cultured in a 30 incubator for 3 to 5 days to prepare a medicinal liquid culture. The liquid medium for culture of the *Monascus* sp. seed culture is preferably a medium obtained by adding 2% to 10% of a rice powder, 0.5% to 2.0% of peptone, 1% to 5% of glycerol, 5% to 20% of glucose (w/v), 1% to 10% of a medicinal natural substrate powder in which percentage % is based on w/v, to distilled water, followed by adjusting an initial pH to 6.0±0.5. Also, a cereal solid sample is inoculated with the liquid culture of *Monascus* sp. at 30±5 in an incubator for 30±5 days to perform solid fermentation and thereby produce a medicinal solid fermentation product containing a higher amount of effective active components. All cultures used for solid fermentation are preferably turned over daily from the second day after fermentation.

In the present invention, what production of statin and ubiquinone, as natural physiologically active substances which are secondary metabolites in liquid and solid media is changed according to *Monascus* genus strains.

According to the present invention, in order to produce mevinolin, *Monascus* sp. is preferably selected from *Monascus anka, Monascus purpureus, Monascus pilosus, Monascus kaoliang* and a combination thereof. Also, in selection of superior strains of the present invention, superior strains that are normally fermented in liquid and solid media and contain both statin and ubiquinone as effective active components are *Monascus anka, Monascus purpureus, Monascus pilosus, Monascus ruber, Monascus araneosus,* and *Monascus kaoliang* strains. In particular, the *Monascus pilosus* strain exhibits a 3.9 to 4.5-fold more effective active compound than other strains and is thus considered to be the most suitable superior strain for liquid and solid fermentation.

Hereinafter, the present invention will be described in detail with reference to examples. These examples are provided only for better understanding and should not be construed as limiting the scope and spirit of the present invention.

EXAMPLE 1

Preparation of Seed Culture

Test Materials and Reagents

All natural substances used for preparation of naturally fermented pharmaceutical composition were commercially obtained in Garak-dong, Seoul, Korea. All solvents such as ethanol or hexane used for extraction of ubiquinone and mevinolin compounds were are solvents for HPLC grade (Fisher Co., USA). Standard mevinolin (lactone form), citrinin and ubiquinone (CoQ10, CoQ9) were commercially obtained from Sigma cooperation (St. Louis, Mo., USA), an acid-form mevinolin (hereinafter, referred to as "mevinolinic acid") was prepared by modifying alkali hydrolysis as disclosed in Friedrich J. et al., J. Chromatogr. A. 704: 363-367 1995. That is, 0.1M NaOH was added to a standard form of mevinolin, heated at 50° C. for one hour, 1M HCl was added thereto to adjust pH to 7.7, and the resulting solution was filtered (0.22 μm, Millipore Co., Bedford, Mass., USA) and was analyzed by HPLC (JASCO PU-987 pump, Tokyo, Japan). Separation of the standard form of mevinolin, mevinolinic acid and citrinin was confirmed through UV spectra ($\lambda$max) and retention time ($t_R$) and quantitative analysis was performed in accordance with calibration curve of standard substances. Separation and quantitative analysis of ubiquinone were carried out using an LC-MS equipped with electrospray ionization (ESI).

Used Strains and Media

Identified 15 species of genus *Monascus* strains were obtained from the Korea Food Research Institute and were used for selection of superior strains. First, all strains were cultured in PDA media (potato dextrose agar; Difco, MI, USA) at 30° C. for 5 days, and a suspension of spores was homogenized and a seed culture was directly inoculated with the same.

Preparation of Selected Seed Culture

Various nutriment medium solutions that have been widely used as nutriment media for solid fermentation were modified and prepared as shown in Table 1. The prepared medium solutions were inoculated with respective strains separated from the primary culture, cultured in a culture incubator at 30° C. for 3 to 5 days, strains were harvested and lyophilized, and contents of statin and ubiquinone were extracted and quantified, or the statin and ubiquinone were used as seed culture media for solid fermentation.

TABLE 1

Composition of natural liquid medium for biosynthesis of ubiquinone and statin

| Nutrients[1] | A[2] | B | C | D | E |
|---|---|---|---|---|---|
| Rice powder | 3.0 | 3.0 | 3.0 | 3.0 | 3.0 |
| Glucose | 10.5 | 10.5 | 10.5 | 10.5 | 10.5 |
| Peptone | 1.5 | 1.5 | 1.5 | 1.5 | 1.5 |
| Glycine | 1.5 | 1.5 | 1.5 | 1.5 | 1.5 |
| Meat extract | 0.1 | 0.1 | 0.1 | 0.1 | 0.1 |
| Ginseng powder | | 1.5 | 1.5 | 1.5 | 1.5 |
| Red paprika powder | | | 1.0 | 1.0 | 1.0 |
| Mushroom powder | | | | 1.0 | 1.0 |
| Tomato powder | | | | | 1.0 |

[1]Weight/volume: %
[2]Liquid medium type

EXAMPLE 2

Selection of Superior Strains

Extraction and Quantification of Mevinolin and Mevinolinic Acid 1.0 mL of a solvent such as methanol or 70% ethanol, 0.1% $H_3PO_4$ acetonitrile was added to 0.1 g of a liquid culture and a solid fermentation product power, and strains were fractionized using an ultrasonicator (Sonic & Materials Inc. USA) at 50° C. for two hours and centrifuged at 12,000 g for 10 minutes. The supernatant was filtered (0.45 µm), and the content of secondary metabolites was measured using HPLC, a Capcell Pak C18 UG120 column (250×4.6 mm, SHISEIDO CO., Tokyo, Japan) was used for HPLC. A solvent for mobile phase was a mixture of acetonitrile and 0.1% $H_3PO_4$ at a ratio of 65:35 (v/v), and elution was performed at a flow rate of 0.8 ml/min. Searching of two compounds was simultaneously carried out at 238 nm, a maximum wavelength of respective compounds. The contents of mevinolin and mevinolinic acid were quantified using a calibration curve made using standard substances of the compounds.

Extraction and Quantification of Ubiquinone 25 ml of water, 70 ml of methanol, 2 g of pyrogallol and 10 g of sodium hydroxide (NaOH) were added to 1.0 g of a liquid culture and a solid fermentation product powder and hydrolyzed in a bath equipped with a reflux condenser at 90 to 95° C. for 30 to 60 minutes. After reaction, the resulting solution was cooled, 50 ml of hexane was added thereto, and the solution was shaken for 5 minutes and was centrifuged to separate the hexane layer. The same process was repeated three times, the collected hexane layer was removed using a vacuum evaporator (40° C.), finally dissolved in isopropanol, filtered through a PTFE membrane filter (0.2 µm), and separated and quantified via LC-MS (Agilent 1100 quaternary pump, Agilent 1100 autosampler, Agilent 1100 column heater, Agilent 1100 UV detector; YMC Pro C18, 3 µm, 2.0×50 mm column, 0.8 mL/min, 5 µL, 275 nm). Quantification of CoQ10 and CoQ9 was carried out by quantifying a ubiquinone substance in samples in accordance with a calibration curve made using a standard substance.

Selection of Superior Strains 15 species of *Monascus* genus strains were cultured in PDA media, respectively, 5-fold sterile water was mixed with strain cultures with a size of 1.5×1.5 cm, was homogenized, 10% (v/w) of the sample weight was harvested and aseptically inoculated in a liquid medium and a solid medium, followed by fermentation for 5 and 30 days livers. Amounts of produced statin, ubiquinone and citrinin were evaluated according to types of *Monascus* strains and the results thus obtained are shown in Table 2.

TABLE 2

Production of statin, ubiquinone and citrinin via culture of *Monascus* strains (liquid fermentation at 30° C. for 5 days)

| Strains | Statin (µg/g DW)[1] | Ubiquinone (µg/g DW) | Citrinin (µg/g DW) |
|---|---|---|---|
| M. anka IFO 478 | 20.2 | 1.5 | ND |
| M. anka IFO 873 | 19.1 | 2.8 | 7.8 |
| M. pilosus IFO 201 | 51.4 | 5.6 | ND |
| M. pilosus IFO 480 | 52.6 | 4.5 | ND |
| M. purpureus ATCC 489 | 45.2 | 2.1 | ND |
| M. purpurea IFO 482 | 35.3 | ND | 3.5 |
| M. ruber IFO 492 | 31.7 | ND | ND |
| M. araneosus IFO 483 | 22.8 | 1.3 | 10.1 |
| M. kaoliang ATCC 592 | 17.9 | ND | 5.7 |
| M. kaoliang ATCC 595 | 44.2 | 1.2 | ND |
| M. kaoliang ATCC 598 | 13.3 | ND | 3.1 |
| M. sp. ATCC 437 | 21.5 | 1.8 | 17.9 |
| M. sp. IFO 301 | 19.2 | 1.1 | ND |
| M. sp. IFO 280 | 16.3 | 1.4 | 6.2 |
| M. vitreus sp. IFO 532 | 27.1 | 1.6 | 4.4 |

ND: Not detected
[1]Mevinolin (ug/g dry weight) = mevinolin (ug/g) and mevinolinic acid (ug/g)
Detection limits of mevinolin, ubiquinone and citrinin are 100 ng/g, 50 ng/g and 100 ng/g, respectively.
All results were averages of n = 3, and analysis was carried out in accordance with the test method described herein.

Strains that did not produce the toxic by-product i.e., citrinin, and contained predetermined levels or higher of amounts of ubiquinone and mevinolin, which were effective metabolites contained in liquid fermentation products, were *M. anka* IFO 478, *M. purpureus* ATCC 489), *M. pilosus* IFO 201, 480, *M. kaoliang* ATCC 595 and other strains (M. sp. IFO 301). In particular, it was confirmed that *M. pilosus* strains were superior strains that exhibited 3.9 to 4.5-fold higher contents of statin and mevinolin, as compared to the remaining strains, and did not produce citrinin while producing the greatest amount of useful metabolites. Also, as can be seen from Table 3, a type of mevinolin present in the *Monascus* sp. bean fermentation product is an active form that contains, as a main component, a mevinolinic acid compound which is an active hydroxycarboxylate, and that has the same structure as the drug such as pravastatin, rather than an inactive lactone form. In draft standard specifications suggested by the Korean Food and Drug Administration regarding the *Monascus* sp. fermentation products, *Monascus* sp. fermentation products should satisfy requirements that the contents of mevinolin and citrinin are 0.05% or more and 50 ppb or less, respectively, so that they can be used for functional health foods.

Accordingly, in order to further improve the content of statin as well as the content of ubiquinone, one of two strains of *Monascus pilosus* selected as superior strains was selected and seed-cultured, cultured in liquid media prepared in five forms shown in Table 1, and growth and proliferation of respective strains were activated to increase contents of statin and ubiquinone. Also, a natural solid medium was inoculated with 10% (v/w) of the selected liquid culture, and the amount of produced effective active substances was measured during fermentation for a predetermined period of time.

EXAMPLE 3

Effects of Seed Culture Composition

Five forms of liquid media (A to E) were prepared and fermented at 30° C. for 5 days. The contents of secondary metabolites and effective active components obtained by fermentation were measured and the results are shown in Table 3. That is, total mevinolin content was 20.5 μg/g, which means that an amount of produced effective active substance is, at most, 2.6-fold lower than other samples using natural medicinal substances. In particular, D form and E form exhibited total mevinolin production amounts of 54.3 and 51.9 μg/g, respectively. The two forms exhibited ubiquinone contents of 28.6 and 28.2 μg/g, respectively, which means that the forms were the most preferred liquid cultures.

As expected, the main component of mevinolin contained in the liquid culture of the present invention was an acid form (hydroxy acid form) of mevinolinic acid (b) and a lactone form of mevinolin (a) was about 8%. The form of natural statin of contained in cultures was a drug that contains about 92% or higher of an active drug and is thus readily absorbed in the body.

TABLE 3

Contents of natural statin and ubiquinone contained
in various forms of liquid cultures

| Type | Mevinolin (μg/g) | | | Ubiquinone (μg/g) | | |
|---|---|---|---|---|---|---|
| | Lactone | Acid | Total | CoQ9 | CoQ10 | Total |
| A | 4.9 | 15.6 | 20.5 | ND | 6.5 | 6.5 |
| B | 3.1 | 32.3 | 35.4 | ND | 15.8 | 15.8 |
| C | 6.7 | 41.2 | 47.9 | 2.7 | 18.7 | 21.4 |
| D | 5.9 | 48.4 | 54.3 | 10.1 | 18.5 | 28.6 |
| E | 6.2 | 45.7 | 51.9 | 11.4 | 16.8 | 28.2 |

All results were averages of n = 3, and analysis was carried out in accordance with the test method described herein.
ND: not detected

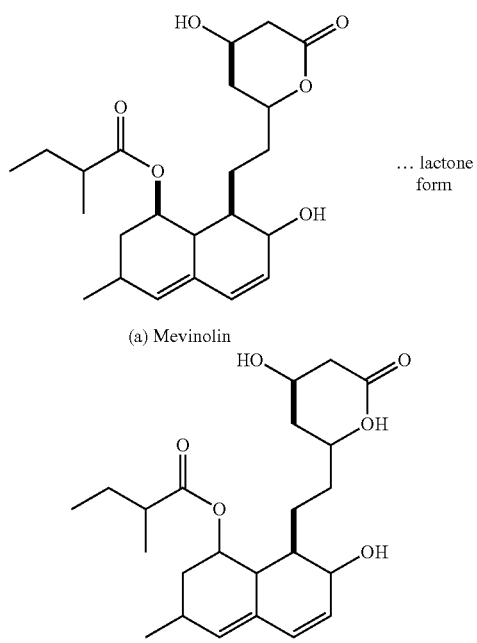

(a) Mevinolin

Hajjaj H. et al. (Appl. Environ. Microbiol. 67: 2596-2602 2001) also emphasized the importance of strain culture conditions since production of secondary metabolites such as lovastatin is considerably varied according to other media and culture conditions. However, to date, research to obtain ubiquinone compounds by fermenting liquid cultures using a medicinal natural substance inoculated with *Monascus* sp. was not found in Korea as well as other nations.

As can be seen from Table 1, the B-form liquid culture has the same composition as the A-form liquid culture in terms of components, other than the *ginseng* powder, that is, rice powder, glucose, peptone, glycine and meat extract. The *ginseng* powder contained in the B form liquid culture and other natural materials such as mushroom and paprika as contained in C, D and E forms were proved to increase the content of natural statin as well as the concentration of ubiquinone. The most preferred form was identified to be a D form and was used as a seed culture in the subsequent solid fermentation. The D form liquid culture was prepared to have a composition in which a rice powder was 3.0%, peptone was 1.5%, glycine was 1.5%, glucose was 10.5%, a meat extract was 0.1%, a *ginseng* powder was 1.5%, red paprika was 1.0% and a mushroom powder was 1.0%, in which percentage(%) is based on w/v, based on the amount of the prepared solution, cultured in a shaking incubator at 30° C. for 5 days and the solid sample was used as a seed culture for fermentation.

EXAMPLE 4

Solid Fermentation Using Only Nonglutinous Rice and Cereal Mixture

Test materials used for solid fermentation were milled nonglutinous rice alone or a mixture of milled nonglutinous rice, barley, wheat, sorghum and millet at a weight ratio of 1:1:1:1:1 (w/w). The test materials were immersed for 10 hours, 100 g of water-removed samples (water content: 35 to 40%) were added to a 500 mL flask, sealed with a natural current and sterilized at 121° C. for 20 minutes. The D form seed culture, among forms of Example 3 cultured in the liquid media, was collected at 10% (v/w) of the sample weight, and a solid medium was aseptically inoculated therewith. The inoculated sample was fermented in a 30° C. incubator for 40 days and fermented samples were collected at respective times, that is, after 5, 10, 15, 20, 25, 30 and 40 days of fermentation, contents of statin and ubiquinone were assayed, the content variation of metabolites according to fermentation time was observed, and results are shown in Table 4. At this time, all cultures were turned over once daily from the second day after culture and the collected samples were lyophilized, powdered and stored in a freezer before use. As a result of testing, it was confirmed that synthesized two physiologically active substances exhibited maximum statin and ubiquinone contents, 791.5 μg/g DW and 250.1 μg/g DW, respectively, based on sample dry weight (DW), at the 30$^{th}$ day of fermentation time, and natural statin exhibited a 13% or more increase in yield, as a result of fermentation in the samples of the present invention, as compared to a common yield of 700 μg/g DW or less.

TABLE 4

Contents of natural statins and ubiquinones in solid cultures
(rice and cereal mixture fermentation products)

| Fermentation time (day) | Statin (lactone + acid) (μg/g dry weight) | | Ubiquinone (CoQ9 + CoQ10) (μg/g dry weight) | |
|---|---|---|---|---|
| (30 ± 5° C.) | Cereal mixture | rice | Cereal mixture | Rice |
| 5 | 92.1 | 57.1 | 80.8 | 0.7 |
| 10 | 186.4 | 121.6 | 120.4 | 2.1 |
| 15 | 472.2 | 256.2 | 168.6 | 8.8 |

TABLE 4-continued

Contents of natural statins and ubiquinones in solid cultures
(rice and cereal mixture fermentation products)

| Fermentation time (day) | Statin (lactone + acid) (μg/g dry weight) | | Ubiquinone (CoQ9 + CoQ10) (μg/g dry weight) | |
|---|---|---|---|---|
| (30 ± 5° C.) | Cereal mixture | rice | Cereal mixture | Rice |
| 20 | 673.6 | 326.5 | 247.8 | 10.4 |
| 25 | 625.8 | 412.8 | 231.6 | 17.6 |
| 30 | 791.5 | 366.7 | 250.1 | 14.2 |
| 40 | 745.2 | 389.2 | 214.6 | 15.3 |

All results were averages of n = 3, and analysis was carried out in accordance with the test method described herein.

Regarding the amounts of medicinal substance produced in solid media, contents of natural statin and ubiquinone were increased by 1.9 times and 14.2 times, respectively, when a homogeneous cereal mixture was used, rather than when rice was used alone. In particular, the amount of produced ubiquinone exhibited remarkable increase in the cereal mixture. Accordingly, it was considered that, as a substrate to produce two compounds having pharmaceutical efficacies, a solid medium using a combined cereal is more preferable than a solid medium using a single cereal.

It could be seen from these results that individual trace components and nutrient components contained in cereals other than rice affected maximum growth of *Monascus* strain cells or increase in biosynthesis of the two physiologically active substances.

EXAMPLE 5

Effects of Fermentation Time

A liquid culture (Type D, pH 6, *M. pilosus* IFO 480) was added as a seed culture medium to the solid medium of Example 4 at an amount of 10% of the sample weight (v/w) and fermented at 30° C. in an incubator for 30 days. As a result, after fermentation for 30 days based on the dry sample, statin content was 791.5 μg/g, and ubiquinone content was 250.1 μg/g. As compared to the liquid fermentation product, both compounds were increased by 8.7 times and 14.6 times, respectively. This demonstrated that that the amount of produced bioactive metabolites was greatly increased, when the solid medium was inoculated with medicinal liquid media, followed by fermentation (Table 4). Overall, as fermentation time passed, amounts of produced ubiquinone and mevinolin increased. The amounts of produced compounds were similarly increased or decreased. After fermentation for 30 days, statin and ubiquinone were measured at 0.079% and 0.025%, respectively, after fermentation for 25 days, the contents were slightly decreased, but production was not stopped, until fermentation was finished. Generally, an amount of statin produced via biosynthesis was known to be varied according to used strains (Bang I Y et al., Korean J. Food Sci. Technol. 35: 442-446 2003) and growth and proliferation conditions (Kwak E J, Cha S K, Lim S I. Korean J. Food Sci. Technol. 35: 830-834 2003; Hajjaj H. et al., Appl. Environ. Microbiol. 67: 2596-2602 2001). That is, when strains exhibited maximum growth depending on the type of media, production of secondary metabolites also reached a maximum level.

Regarding the statin compound detected from the solid fermentation product of the present invention, an acid form was more stable than a lactone form under water-alcohol conditions. Accordingly, the solid fermentation product using *Monascus pilosus* strains contains 0.07% in average of natural statin that is an inhibitor of synthetic enzymes (HMG-CoA reductase) of endogenous cholesterol and 200 to 250 μg/g in average of ubiquinone capable of inhibiting complications of statin, based on the weight of dry product.

The present invention provides natural liquid cultures and solid fermentation products containing statin compounds, as natural anti-cholesterol substances, and ubiquinone compounds which may be deficient due to long-term use of statin, using *Monascus* sp. which were not developed in Korea as well as other nations to date and furthermore, safely provides a functional health food or a pharmaceutical natural composition containing a high-value multi-physiologically active substance, in addition to the components, thus exerting potent efficacies distinguished with conventional synthetic medicines.

INDUSTRIAL APPLICABILITY

The present invention prepares and provides statin and ubiquinone as combined physiologically active substances using *Monascus* sp. and natural substances, thus being useful in the functional health food or biomedicine industries.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for producing a liquid culture of *Monascus* sp. comprising:
   inoculating a liquid medium comprising one or more natural substance powders having a molecular structure containing an isoprene unit or a benzoquinone nucleus, a rice powder, glucose, peptone, glycine, a meat extract and distilled water, with the genus *Monascus* sp., followed by shake culturing at 30° C., to simultaneously biosynthesize natural mevinolin and ubiquinone compounds, wherein the one or more natural substance powders comprises a *ginseng* powder, a red paprika powder, a mushroom powder, a tomato powder, or a combination thereof.

2. The method according to claim 1, wherein the *Monascus* sp. is selected from *Monascus anka, Monascus purpureus, Monascus pilosus, Monascus ruber, Monascus araneosus, Monascus kaoliang* ATCC 595, *Monascus vitreus* sp. IFO 301 genus and a combination thereof.

3. The method according to claim 1, wherein the *Monascus* sp. is a superior strain selected from *Monascus purpureus* sp. IFO 202, and *Monascus purpureus* sp. IFO 480.

4. The method according to claim 1, wherein the liquid culture is cultured by inoculating a seed culture of *Monascus* sp. cultured in potato dextrose agar (PDA).

5. The method according to claim 1, wherein the liquid medium comprises 2 to 10% of a rice powder, 0.5 to 2.0% of peptone, 1 to 5% of glycine, 6 to 20% of glucose, 0.1 to 1.0% of a meat extract, 0.5 to 1.5% of a *ginseng* powder, 0.5 to 1.5% of a red paprika powder, 0.5 to 1.5% of a mushroom powder and the balance of distilled water, in which percentage % is based on w/v, and an initial pH of the liquid medium is adjusted to 6.0±0.5.

6. The method according to claim 5, wherein the liquid medium further comprises 0.5 to 1.5% (w/v) of a tomato powder.

* * * * *